United States Patent [19]

Schreck

[11] Patent Number: 5,281,751
[45] Date of Patent: Jan. 25, 1994

[54] SYNERGISTIC PRODUCTION OF CARBOXYLIC ACIDS FROM ALCOHOLS

[75] Inventor: David J. Schreck, Cross Lanes, W. Va.

[73] Assignee: Union Carbide Chemicals and Plastics Company Inc., Danbury, Conn.

[21] Appl. No.: 998,423

[22] Filed: Dec. 29, 1992

Related U.S. Application Data

[63] Continuation of Ser. No. 533,599, Jun. 5, 1990, abandoned, which is a continuation of Ser. No. 434,475, Nov. 14, 1989, abandoned, Ser. No. 434,476, Nov. 14, 1989, abandoned, and Ser. No. 434,477, Nov. 14, 1989, abandoned, which is a continuation of Ser. No. 793,447, Oct. 28, 1985, abandoned, which is a continuation-in-part of Ser. No. 557,274, Dec. 2, 1983, abandoned, said Ser. No. 434,475, is a continuation of Ser. No. 793,444, Oct. 28, 1985, abandoned, which is a continuation-in-part of Ser. No. 557,272, Dec. 2, 1983, abandoned, said Ser. No. 434,476, is a continuation of Ser. No. 787,720, Oct. 17, 1985, abandoned, which is a continuation-in-part of Ser. No. 557,268, Dec. 2, 1983, abandoned.

[51] Int. Cl.$^5$ ............................................. C07C 51/12
[52] U.S. Cl. ..................................... 562/519; 562/406
[58] Field of Search ................. 562/519, 406; 560/243

[56] References Cited

U.S. PATENT DOCUMENTS

| | | | |
|---|---|---|---|
| 3,769,329 | 10/1973 | Paulik et al. | 560/232 X |
| 4,733,006 | 3/1988 | Singleton et al. | 562/519 |
| 4,792,620 | 12/1988 | Paulik et al. | 560/232 |
| 5,001,259 | 3/1991 | Smith et al. | 562/519 |
| 5,214,203 | 5/1993 | Koyama et al. | 562/519 |

*Primary Examiner*—Arthur C. Prescott
*Attorney, Agent, or Firm*—Brooks Haidt Haffner & Delahunty

[57] ABSTRACT

A process for the production of an aliphatic carboxylic acid of the formula RCOOH, wherein R is an alkyl group having from 1 to 5 carbon atoms, comprises the catalytic reaction of an alcohol of formula ROH and carbon monoxide in the presence of a rhodium catalyst, methyl iodide, a high lithium iodide content, a low water content and an organic ester of formula $RCO_2R$. The process can optionally be carried out in the presence of hydrogen and/or an organic ligand of formula $ER^{11}_3$ where E is nitrogen, phosphorus, arsenic, antimony or bismuth and $R^{11}$ is an organic moiety.

17 Claims, No Drawings

SYNERGISTIC PRODUCTION OF CARBOXYLIC ACIDS FROM ALCOHOLS

This application is a continuation of application Ser. No. 07/533,599 filed Jun. 5, 1990 now abandoned which is a continuation of three prior applications of the same inventor. The subject matter described and claimed in the three applications have been combined in this case. Accordingly, said application is a continuation of Ser. No. 07/434,475 filed on Nov. 14, 1989 now abandoned which is a continuation application of Ser. No. 06/793,444 filed on Oct. 28, 1985, now abandoned, which, in turn, is a continuation-in-part of application Ser. No. 06/557,272, filed Dec. 2, 1993, now abandoned.

Said application is also a continuation of application Ser. No. 07/434,476 filed Nov. 14, 1989, now abandoned which is a continuation of application Ser. No. 06/787,720 filed Oct. 17, 1985, now abandoned, which in turn is a continuation-in-part of application Ser. No. 06/557,268 filed Dec. 2, 1983, now abandoned.

Said application also is a continuation of application Ser. No. 07/434,477 filed Nov. 14, 1989, now abandoned which is a continuation of application Ser. No. 06/793,447 filed Oct. 28, 1985, now abandoned which in turn is a continuation-in-part of application Ser. No. 06/557,274 filed Dec. 2, 1983 now abandoned.

BACKGROUND OF THE INVENTION

The production of organic compounds using carbon monoxide or synthesis gas, which is a mixture of carbon monoxide and hydrogen, as reactant has been known for a significant period of time. It is well known that one can produce methanol directly from synthesis gas and that methanol can be further reacted by hydroformylation, homologation and carbonylation reactions to produce acetaldehyde, ethanol and acetic acid or its methyl ester, respectively. It is also know that esters, ethers, and other organic compounds can be reacted with carbon monoxide or synthesis gas to produce oxygenated organic compounds. The difficulties, however, have resided in the ability to carry out any one of these chosen reactions to produce the desired compound at acceptable efficiency, conversion rate and selectivity.

In almost all instances the reaction is generally catalysed using a Group VIII transition metal compound as catalyst and a halogen as the promoter. It is known that many other metal compounds and promoters can be used. In addition, the prior art has disclosed the use of secondary activators or ligands in conjunction with the metal catalysts and promoters. These secondary activators can be other metallic salts or compounds, amines, phosphorus compounds, as well as a multitude of other compounds that have been disclosed in the published literature. Thus, a typical catalyst system contains the metal atom catalyst, promoter and, optionally, ligands, solvents and secondary activators. Though a significant amount of literature does exist describing the production of oxygenated compounds by the isomerisation of methyl formate, to our knowledge it does not disclose or suggest our invention. Several of the pertinent patents in this area are discussed below.

French Patent No. 2,317,269, filed by Compagnie Des Metaux Precieux and published on Feb. 4, 1977, discloses the production of aliphatic carboxylic acids by the reaction of an alcohol with carbon monoxide in the presence of a catalyst containing at least three essential components, iridium atom, copper atom and halogen. This is not our process.

In European Patent Application No. 0018927; filed by Gauthier-Lafaye et al on Apr. 23, 1980 and published on Nov. 12, 1980, there is described a process for the production of monocarboxylic acids by the carbonylation of an alcohol using a nickel catalyst, a halide and a solvent; in this reference synthesis gas is used.

In European Patent Application No. 0045637, filed by Pruett on Jul. 31, 1981 and published on Feb. 10, 1982, there is disclosed the direct conversion of formic acid esters to their corresponding carboxylic acids without the presence of carbon monoxide using as catalyst a soluble iridium salt and an iodine promoter. This is not our catalytic process.

Another known procedure for producing acetic acid is the catalytic isomerisation of methyl formate as shown by the reaction:

$$CH_3OOCH \rightarrow CH_3COOH$$

This procedure is shown in U.S. Pat. No. 1,697,109, issued to Henry Dreyfus on Jan. 1, 1929. The process described is a vapour phase isomerisation reaction carried out at 200° C. to 450° C. at a pressure up to 200 atmospheres using a metal oxide or acetate catalyst. It does not disclose the use of rhodium and lithium iodide plus optionally methyl iodide or alcohols as starting materials.

U.S. Pat. No. 2,508,513, assigned to Celanese Corporation and issued on May 23, 1950 claims an iron metal atom based catalyst, e.g. nickel, promoted with methyl iodide for the isomerisation of methyl formate to acetic acid, carried out at 300° C. to 400° C. and a pressure up to 400 atmospheres. Carbon monoxide may be present. It does not disclose the use of rhodium and lithium iodide plus methyl iodide nor of alcohols as starting materials.

U.S. Pat. No. 3,060,233, issued to Hohenschutz on Oct. 23, 1962, discloses the carbonylation of methanol to acetic acid using a metal of the iron group of the Periodic Table and a halide. It does not disclose use of rhodium.

U.S. Pat. No. 3,769,329, issued Oct. 30, 1973 to Paulik et al, discloses the production of carboxylic acids from alcohols, or the ester, ether and halide derivatives thereof, and carbon monoxide using a rhodium catalyst and a halogen component. It does not mention lithium iodide or mixtures of lithium iodide and methyl iodide. The process disclosed in this reference requires the use of acidic halogen compounds which are corrosive and difficult to handle. High levels of methyl iodide are used and recycled in order to maintain activity. Further, the preferred mode of operation of this process uses a large excess of water to ensure selectivity to acetic acid.

U.S. Pat. No. 3,798,267, issued Mar. 19, 1974, relates to the conversion of methyl formate to acetic acid in the presence of a catalyst system consisting essentially of activated carbon and a halogen promoter. The reference uses catalyst and starting materials different than those employed in the invention of this application.

U.S. Pat. No. 4,194,056, filed by Antoniades and issued Mar. 18, 1980, discloses the production of carboxylic acid from methyl formate using a soluble rhodium catalyst, halogen promoter and carbon monoxide. This is not the process of the instant invention, nor does this reference suggest or disclose the use of lithium iodide or a mixture of lithium iodide plus methyl iodide and the unexpected results achieved by such use.

U.S. Pat. No. 4,212,989, issued to Isshiki et al on Jul. 15, 1980, describes a process for producing carboxylic acids or their esters by reacting an alcohol or an ether with carbon monoxide using a Group VIII metal catalyst and an iodine promoter. The reference contains no suggestion or disclosure of the production of organic carboxylic acids by the process of our invention.

British Patent Specification 1,286,224, issued Aug. 23, 1972 to Wakamatsu et al, relates to the reaction of methyl formate with carbon monoxide in contact with a rhodium catalyst and a halogen promoter to produce acetic acid. It contains no recognition of the distinct advantages achieved with the use of lithium iodide with or without methyl iodide, in fact it does not mention mixtures of these specific compounds.

British Patent Specification 1,293,193, issued Oct. 18, 1972 to Japan Gas-Chemical Company Inc, relates to the direct conversion of formic acid esters to the corresponding carboxylic acids, in the presence of carbon monoxide, a catalyst that is a Group IIb or VIII metal and an organic polar solvent. It does not disclose use of rhodium atom plus lithium iodide with or without methyl iodide.

Japanese Patent Publication 50-16773, filed by Kuraishi et al and published on Jun. 16, 1975, discloses the production of an organic acid from the corresponding formic acid ester in the presence of carbon monoxide using a catalyst system containing cobalt, iron or mercury and a halogen plus an alkali metal salt of a lower aliphatic carboxylic acid, triamine or cyclic amine.

Japanese Patent Publication 51-65703, filed by Mitsui Petrochemical and published on Jun. 7, 1976, discloses the reaction of methyl formate in the presence of carbon monoxide using a system containing a rhenium catalyst and halogen compound to produce acetic acid.

Japanese Patent Publication 56-22745, filed by Wada et al and published Mar. 3, 1981, discloses the isomerisation of a formic acid ester to the corresponding acid in the presence of carbon monoxide, palladium atom, halogen and base.

Japanese Patent Application No. 56-73040, filed by Isshiki et al and published on Jun. 17, 1981, relates to a process for producing acetic acid by isomerising methyl formate in the presence of carbon monoxide using a nickel catalyst, an iodine compound and an organic nitrogen compound.

Japanese Patent Application 56-83439, filed by Isshiki et al and published Jul. 8, 1981, discloses a method for producing acetic acid by heating methyl formate and carbon monoxide in contact with a catalyst containing palladium, ruthenium and/or iridium metal atom and a halide promoter.

None of the five Japanese Patent Applications disclose a process for producing acetic acid from an alcohol or a formate ester using a catalyst mixture consisting essentially of rhodium metal atom and lithium iodide with or without methyl iodide.

It can be seen that the prior art contains many disclosures dealing with the catalytic production of acetic acid. The art also discloses the production of other organic carboxylic acids by other methods. One of the disadvantages in many of these reactions is the presence of water with the eventual need to remove it from the desired organic acid product. This removal is both complicated and costly. Other disadvantages often include the simultaneous occurrence of other reactions leading to the formation of by-products, such as, dimethyl acetal, methyl acetate, ethanol etc. These reactions compete with the organic acid production resulting in low conversion rate and selectivity to organic acid.

Many processes employed for the production of organic acids use a catalyst system containing a source of metal atom and a source of halide atom. The alkali metal halides are often mentioned as suitable halide sources, but no distinction is made between any specific one of the alkali metal halides or between any other halogen compound. Nor do any of the references suggest or recognize the synergistic advantage of the use of mixtures of lithium iodide and methyl iodide in conjunction with rhodium catalyst.

SUMMARY OF THE INVENTION

A catalyst system and process for the production of organic acids at high efficiency, selectivity and conversion rate by the reaction of mixtures of alcohol and an ester or a compound which under the reaction conditions can be converted to an ester (e.g. acetic acid, acetic anhydride, methyl formate) and carbon monoxide has been found. The catalyst system charged to the reactor in our process contains rhodium atoms, lithium iodide and optionally methyl iodide and an organic ligand. The use of lithium iodide and optionally methyl iodide in this system within the ranges defined results in a synergistic effect with unexpectedly high efficiency, high conversion rate or activity and high selectivity not heretofore achieved.

Furthermore, the use of lithium iodide and hydrogen in this system within the ranges defined also results in unexpectedly high efficiency, high conversion rate or activity and high selectivily not heretofore achieved.

DESCRIPTION OF THE INVENTION

In the catalytic reactions of synthesis gas or carbon monoxide in processes to produce oxygenated organic compounds, there are several criteria required of the catalyst. The catalyst must be as stable as possible, it should have a high activity or conversion rate and it should have as high a selectivity for the desired product as possible.

Stability of the catalyst relates to how long the catalyst remains functional before either breaking down or losing its catalytic effect.

Activity or conversion rate relates to the amounts of reactants the catalyst converts to product per unit of time, generally expressed in g.mole per liter per hour (g mole/l/hr).

Selectivity relates to the quantity of desired product produced, generally expressed in mole percent, based on the total amount of both desired products and undesired products produced.

The goal to be achieved is high values for all three criteria and continued efforts are being made to find new catalyst compositions to reach this goal without having a significant detrimental effect on the overall process. Toward this goal the prior art has developed catalyst systems containing a wide variety of metal atoms, promoters and activators, in many cases with diverse other components added. Though these catalyst systems are effective, improvement is always desirable.

The present invention is based on the unexpected and unpredictable discovery that the rhodium-lithium iodide system, optionally in the presence of methyl iodide or hydrogen, in conjunction with an ester or a compound which under the reaction conditions can be converted to an ester is an unexpectedly superior catalystic system showing a synergistic effect for the production of organic acids from alcohols at unexpected high efficiency, selectivity and conversion rate. It was also found that a ligand, $ER''_3$, can also be present as an optional component of the system. This unexpected synergistic improvement in efficiency, selectivity and conversion rate is achieved when the rhodium catalysed system's components are maintained within a defined range and when lithium iodide and optionally methyl iodide are present as the source of the halogen component in the system, optionally with hydrogen. A solvent and/or diluent can also be present if desired. The improved catalyst system of this invention can be portrayed as containing the components $Rh$-$LiI$-$CH_3I$-$ER''_3$, wherein $Rh$ is the rhodium containing compound and $CH_3I$ and $ER''_3$ are optionally present. Also present in the system is an ester or a compound which under the reaction conditions can be converted to an ester.

In the process of our invention, alcohols are reacted with carbon monoxide in the presence of an ester or ester-forming compound using a particular catalyst system containing rhodium atoms and lithium iodide and optionally methyl iodide. This system synergistically produces commercially desirable organic acids at unexpectedly high efficiency, conversion rate and selectivity, with a minimum of by-products and without the presence of water. The overall reaction that occurs is theoretically:

$$ROH + CO \rightarrow RCOOH$$

In the above formula, R is a monovalent hydrocarbyl group. It can be an alkyl group having from 1 to 30 carbon atoms, preferably from 1 to 15 carbon atoms, and most preferably from 1 to 5 carbon atoms; an alkenyl group having from 2 to 30 carbon atoms, preferably from 2 to 15 carbon atoms and most preferably from 2 to 5 carbon atoms; or an aryl, aralkyl or alkaryl group having 6 to 10 ring carbon atoms, e.g. phenyl and naphthyl, with from 1 to 10 carbon atoms, preferably 1 to 4 carbon atoms, in the alk-moiety thereof. The R group can be linear or branched and it can be unsubstituted or substituted with groups which will not have an adverse effect on the reaction; further; the alkenyl groups can contain more than one unsaturated bond.

Illustrative of suitable alcohols one can mention methanol, ethanol, the propanols, the butanols, the decanols, 2-ethylhexanol, benzyl alcohol, vinyl alcohol, allyl alcohol.

The rhodium component of the catalyst system can be supplied from any number of sources, many of these are known to those of ordinary skill in the art. Thus, it is not necessary for an understanding thereof to specifically enumerate every suitable type and every specific compound since any of the known rhodium compounds can be used.

The essential rhodium component of the catalyst system of the present invention may be provided by introducing into the reaction zone a compound of rhodium or may be provided by introducing into the reaction zone rhodium. Among the materials which may be charged to the reaction zone to provide the rhodium component of the catalyst system of the present invention are rhodium metal, rhodium salts and oxides, organo rhodium compounds, coordination compounds of rhodium and the like. Specific examples of materials capable of providing the rhodium constituent of the catalyst system of the present invention may be taken from the following non-limiting partial list of suitable materials:

$RhCl_2$
$RhBr_3$
$RhI_2$
$RhCl_3 \cdot 3H_2O$
$RhBr_3 \cdot 3H_2O$
$Rh_2(CO)_4Cl_2$
$Rh_2(CO)_4Br_2$
$Rh_2(CO)_4I_2$
$Rh_2(CO)_8$
$Rh[(C_6H_5)_3P]_2(CO)I$
$Rh[(C_6H_5)_3P]_2(CO)Cl$
Rh metal
$Rh(NO_3)_3$
$RhCl[(C_6H_5)_3P]_2(CH_3I)_2$
$Rh(SnCl_3)[(C_6H_5)_3P]_2$
$RhCl(CO)[(C_6H_5)_3As]_2$
$RhI(CO)[(C_6H_5)_3Sb]_2$
$[(n-C_4H_9)_4N][Rh(CO)_2X_2]$ where $X = Cl-$, $Br-$, $I-$
$[(n-C_4H_9)_4As]_2[Rh(CO)_2Y_4]$ where $X = Br-$, $I-$
$[(n-C_4H_9)_4P][Rh(CO)I_4]$
$Rh[(C_6H_5)_3P]_2(CO)Br$
$Rh[(n-C_4H_9)_3P]_2(CO)Br$
$Rh[(n-C_4H_9)_3P]_2(CO)I$
$RhBr[(C_6H_5)_3P]_3$
$RhI[(C_6H_5)_3P]_3$
$RhCl[(C_6H_5)_3P]_2$
$RhCl[(C_6H_5)_3P]_3H_2$
$[(C_6H_5)_3P]_3Rh(CO)H$
$Rh_2O_3$
$[Rh(C_3H_4)_2Cl]_2$
$K_4Rh_2Cl_2(SnCl_2)_4$
$K_4Rh_2Br_2(SnBr_3)_4$
$K_4Rh_2I_2(SnI_2)_4$ In addition, one can use the other Group VIII transition metals comprising the iron triad, i.e. iron, ruthenium, osmium; the cobalt triad, i.e. cobalt, rhodium, iridium; or the nickel triad, i.e. nickel, palladium, platinum. Though these will catalyse the reaction, the preferred metals are nickel and rhodium, with the most preferred being rhodium.

The rhodium or Group VIII metal atom concentration can vary over a wide range. Enough metal atom must be present to achieve reasonable reaction rates; however, an excess may on occasion result in undesired by-products formation. For simplicity, the rhodium atom will be used in the specification with the understanding that it also applies to the other transition metals of Group VIII. The mole ratio of rhodium to alcohol can vary from 1:25 to 1:4,000, the preferred range is from about 1:40 to 1:2,000, with the most preferred range being from about 1:100 to 1:1,000. The amount used is not a critical feature in this invention and higher rhodium concentrations are acceptable but are influenced by economic considerations.

The second component of the catalyst system is lithium iodide. It can be charged directly or it can be formed in situ by any combination of lithium compound and iodine component that will result in the formation of lithium iodide during the reaction. Lithium bromide can also be used but the iodide is preferred. The presence of lithium iodide or lithium bromide in conjunction with methyl iodide is a critical feature of an embodiment of this invention. Direct charge of lithium iodide is the preferred form. However, any convenient combination of compounds for in situ formation of lithium iodide can be used. This includes the use of lithium carboxylates, carbonates and the like with a halogen compound such as iodine or an alkyl halide. A suitable combination for in situ formation is lithium carboxylate and an alkyl halide.

The third an optional component of the system is methyl iodide, which can be added directly or formed in situ by the use of hydrogen iodide, which reacts to produce methyl iodide. The $Rh:CH_3I$ mole ratio can vary from 1:1 to 1:1,000, preferably from 1:2 to 1:450, and most preferably from 1:8 to 1:150.

Sufficient lithium iodide and methyl iodide should be present to exert a promoting effect on the reaction and to result in high efficiency, conversion rate and selectivity to the corresponding organic acid. The mole ratio of $Rh:LiI$ can vary over a wide range. A $Rh:LiI$ mole ratio of from 1:1 to 1:1000 can be employed, the preferred range is from about 1:2 to 1:450 and most preferably it is from about 1:8 to 1:150. The mole ratio of $LiI$ to $CH_3I$ can vary from 1:1,000 to 1,000:1, preferably from 1:450 to 450:1, and most preferably from 1:150 to 150:1.

As indicated, hydrogen, at specifically recited concentrations, has a particular enhancing effect on reaction or conversion rate that was completely unexpected and unpredictable. It was observed that the addition of hydrogen to the reaction system to maintain a concentration of 1 to 50 mole percent hydrogen in the reactor, based on the moles of carbon monoxide present in the reactor, results in a multi-fold increase in the conversion rate of the alcohol to the corresponding carboxylic acid without any noticeable increase in by-products formation. Higher concentrations lead to more by-products formation. The preferred hydrogen addition is sufficient to maintain a concentration of from 2 to 10 mole percent hydrogen. The hydrogen is initially added to the reactor either as a separate stream or together with the carbon monoxide; make-up amounts can be introduced in the same manner, as needed, to maintain the hydrogen concentration at the concentration defined.

As indicated, an organic ligand of the general formula $ER_3''$ can optionally be present in the reaction system. The use of such ligands is known, as are their identities, to those skilled in this art. In this formula E represents a Group VA element, e.g. N, P, As, Sb and Bi, and $R''$ represents an organic moiety. The ligand can serve as a catalyst stabiliser and/or to further enhance efficiency, conversion rate and selectivity, especially when the reaction is carried out at higher temperatures, for example at about 200° C. or above. The ligand also serves to inhibit equipment corrosion in some instances. However, the use of a ligand is not mandatory and the reaction can be carried out without it.

A large number of organic ligands is known and any of these can be used provided they do not have an adverse effect on the reaction. Among those of particular utility are the tertiary amines and the tri-and pentavelent phosphorus compounds. Though those skilled in the art know these compounds, illustrative of suitable compounds one can mention triethylphosphine, tributylphosphine, tri-2-ethylhexylphosphine, triphenylphosphine, tri(4-methoxyphenyl)phosphine, tri-p-tolylphosphine, tri(3-chlorophenyl)phosphine, diphenyl hexylphosphine, dimethyl (3-methoxyphenyl)phosphine, dibutyl stearylphosphine, tribenzylphosphine, dipropyl phenylphosphine, ethyl dipropylphosphine, tricyclohexylphosphine, cyclohexyl dibutylphosphine, propyl diphenylphosphine, dipropyl phenylphosphine, phenyl diethylphosphine, tridecylphosphine, trioctadecylphosphine, methyl diethylphosphine, ethyl diphenylphosphine, tolyl diethylphosphine, cyclohexyl diethylphosphine, diethyl cyclohexylphosphine, bis-(diphenylphosphino)-ethane, bis-(diethylphosphino)-propane, bis-(diphenylphosphino)-butane, bis-(diethylphosphino)-octane, trimethylamine, triethylamine, tri-n-butylamine, tri-t-butylamine, tri-2-ethylhexylamine, methyl dibutylamine, tridodecylamine, tristearylamine, ethyl dibutylamine, tricyclohexylamine, triphenylamine, tri(4-methoxyphenyl)amine, tri(p-chlorophenyl)-amine, dibutyl phenylamine, dipentyl cyclopentylamine, ethyl diphenylamine, trinaphthylamine, tri-p-tolylamine, tri-benzylamine, tri(3-methylcyclohexyl)amine and the arsines, stibines and bismuthines corresponding to the above identified phosphines and amines. These and many others are known in the art. They can be used singly or, if one desires, mixtures containing two or more ligands can be used. One can also employ a phosphine oxide or phosphite corresponding to the above phosphines as the ligand; these are also well known.

The concentration of ligand charged can vary from a molar ratio of ligand to rhodium of from about 50:1 to 1:50, preferably from 10:1 to 1:10, most preferably about 3:1 to 1:1.

In addition to the ligand one can optionally have a solvent present. Many essentially inert solvents are known as useful, essentially inert, diluents and illustrative thereof one can mention 1,4-dioxane, the polyethylene glycol di-ethers or esters, diphenyl ether, sulfolane, toluene, carboxylic acids as well as any other diluent or solvent which does not interfere with the reaction to any significant extent. The reaction is preferably carried out in the absence of any solvent or diluent other than those required to introduce reactants or catalyst components.

The present invention does not require the use of acidic halogen promoters, it employs the alkali metal halide lithium iodide. Nor does it require the presence of water in the quantities which give a standing water concentration of 12 to 16% by weight in the reaction system as have been previously used in the art. When practising the present invention a low water standing concentration of from 0 to 6.5% by weight can be used thereby facilitating the reaction product. It was surprising, unexpected and unpredictable that a basic iodide, lithium iodide, would convert methanol to acetic acid because Example 15 of U.S. Pat. No. 3,769,329 taught that use of rhodium, water, acetic acid, methanol and the basic iodide potassium iodide showed little, if any, reaction at carbon monoxide pressure of 800 psig and a reaction temperature of 175° C. In this reference, reaction was not observed until the reaction mixture was acidified with a mineral acid, e.g. phosphoric acid. In our invention addition of acid is not required and the basic iodide lithium iodide is used. Under essentially the same conditions of pressure and temperature, a reaction mixture of methanol, methyl acetate, rhodium and lithium iodide produced acetic acid at excellent rates and selectivities; contra to the teachings of U.S. Pat. No. 3,769,329.

Also essential to this invention is the presence in the reaction mixture of an organic ester or of a compound which under the reaction conditions can be converted to an organic ester; thus, for example, materials such as the acids, anhydrides, and even the esters themselves. The presence of hydrogen in said compound is critically important.

Thus, it was observed in the reaction to produce acetic acid from methanol that pure methanol in the absence of methyl acetate or ester forming compound did not react with carbon monoxide in the presence of rhodium atom and lithium iodide at 800 psig and about 180° C. Nor did reaction occur when 1,4-dioxane was used as the solvent. However, the addition of methyl acetate to the reaction mixture resulted in good conversion rates and high selectivity to acetic acid as shown in our examples. The preferred are methyl acetate or compounds which form methyl esters during the reaction.

The reaction is carried out at a temperature of from about 50° C. to 350° C., preferably from 120° C. to 220° C. and most preferably from 150° C. to 200° C. When the reaction is carried out at temperatures above 200° C. in the presence of an $ER''_3$ ligand, the phosphines are the preferred ligands.

The pressure of the reaction can be from about 150 psig to 10,000 psig, preferably from 200 psig to 2,000 psig, most preferably from 500 psig to 1,000 psig.

The reaction time varies depending upon the reaction parameters, reactor size and charge, and the individual components employed at the specific process conditions. The reaction can be a batch or continuous reaction.

The synergistic effect of mixtures of lithium iodide and methyl iodide on conversion rate was completely unexpected and unpredictable. Significant rate increases were obtained as compared to the use of rhodium with lithium iodide alone or rhodium with methyl iodide alone. The significantly enhanced reaction rates in the production of organic acids from alcohols in the presence of an ester or ester-forming compound are very advantageous in that they result in increased productivity from an available reactor, or they would allow for a significant reduction in size for a new reactor. Another advantage is that equivalent productivity can be achieved with the use of much less of the expensive rhodium catalyst. Use of the system of this invention results in production of acetic acid from methanol at typical conversion rates of from 5 to 7.5 gmoles/1/hr and typical selectivities of from 95% to 99% at 180° C. and 500 psig CO pressure. In the case of mixtures of lithium iodide and methyl iodide the values obtained exceed those obtained when either methyl iodide or lithium iodide were used individually with rhodium.

The experiments and examples detailed below were carried out in a Hasteloy (registered trade mark) steel autoclave reactor having a volume of 300 ml, which was equipped with temperature and pressure sensing means, heating and cooling means, agitator and inlet and outlet means for introducing and removing components from the reactor. The autoclaves used in synthesis gas reactions are well known in the art and can be used in this process.

Prior to charging the reactants the autoclave was washed with methanol at 100° C. under a nitrogen gas pressure of 500 to 1,000 psig by agitating for 30 minutes. The autoclave was drained, rinsed with dry acetone, and dried with nitrogen. The liquid components were charged to the cleaned autoclave first and then the solid components were added and stirred. The autoclave was closed and purged with carbon monoxide and then pressurised to the desired pressure with carbon monoxide. The autoclave contents were heated to the selected temperature, with agitation (usually 750 rpm), in about 45 minutes. After the desired temperature was reached, the reaction was allowed to consume carbon monoxide for the time period indicated. During this period the pressure was maintained by addition of carbon monoxide as needed.

At the end of the reactor run, the contents were cooled, generally to about 10° C. A vapour phase sample was taken for gas chromatography analysis, the gas phase was vented through two dry-ice acetone traps and then through a 10 liter saturated solution of calcium hypochlorite to remove metal carbonyls, if formed. The reactor was pressurised three times with nitrogen, 90 psig and vented through the same system.

The residual reactor contents were dumped into a chilled pressure bottle and sealed. Subsequent analysis was performed using a Hewlett Packard Model 5880 gas chromatograph equipped with a one eighth inch diameter by ten feet long column packed with Chromosorb 101.

The following Examples serve to further illustrate this invention. In the Examples, the term "AcAc" means "acetylacetonate". Values given for acetic acid obtained include acetic acid equivalents present as methyl acetate.

EXAMPLE 1

In this experiment the system contained rhodium atom and lithium iodide only.

The autoclave was charged with 2.06 g of $Rh(CO)_2$ AcAc (8 mmoles), 8.57 g of lithium iodide (64 mmoles), 50 ml of methanol (1.25 moles) and 100 ml of methyl acetate. Following the procedure described above the reaction was carried out at 180° C. and a carbon monoxide pressure of 1,000 psig for 5 hours. The major product was 1.25 moles of acetic acid. The calculated rate to acetic acid was 2.4 gmole/1/hr and the conversion of methanol to acetic acid was 100% at the time the reaction was arbitrarily terminated.

Control Experiment A

In this experiment, not illustrative of the invention, the system contained rhodium atom and methyl iodide only.

The autoclave was charged with 2.1 g of $Rh(CO_2)$ AcAc (8 mmoles), 9.1 g of methyl iodide (64 mmoles), 50 ml of methanol and 100 ml of methyl acetate and reacted at 800 psig in the same manner as Example 1 for 4 hours. Major product was 0.49 mole of acetic acid. The calculated rate to acetic acid was 0.86 gmole/1/hr and the conversion of methanol to acetic acid was 40% at the time the reaction was arbitrarily terminated.

EXAMPLE 2

In this example, illustrative of the invention, the autoclave was charged with 1.1 g of $Rh(CO)_2$ AcAc (4 mmoles), 4.2 g of lithium iodide (32 mmoles), 4.6 g of methyl iodide (32 mmoles), 50 ml of methanol (1.25 moles) and 100 ml of methyl acetate. The procedure followed was the same as described in Example 1 at a pressure of 600 psig. After 3 hours all of the methanol had been converted to acetic acid. The calculated rate to acetic acid was 2.2 gmole/1/hr at the time the reaction was arbitrarily terminated and the conversion of methanol to acetic acid was 100%.

Comparison to Example 1 shows significantly lower Rh concentration required to achieve the same results, comparison to Control Experiment A shows significantly better reaction rate and conversion.

EXAMPLE 3

The autoclave was charged with 1 mmole of rhodium dicarbonyl acetylacetonate, 100 mmoles of lithium iodide, 50 ml of methanol and 100 ml of methyl acetate. The reactor was pressurised with carbon monoxide enriched with 5 mole percent hydrogen to a total pressure of 800 psig at 180° C. and maintained at those conditions for 4 hours. During this period carbon monoxide alone was added to the reactor to maintain the pressure. Analysis of the products at the conclusion established that 75.4% of the methanol charged had been converted to acetic acid at a selectivity greater than 95%. The reaction was proceeding at a conversion rate of 2.2 gmole/l/hr at the time the experiment was arbitrarily terminated, that is after 4 hours of reaction.

For comparative purposes, the reaction was repeated but in this instance the hydrogen was not added. Under the same conditions 20.4% of the methanol charged was converted to acetic acid. The reaction was proceeding at a conversion rate of 0.33 gmole/l/hr at the time the experiment was arbitrarily terminated after 5 hours.

Comparison of the results obtained show the unexpected and unpredictable increase in conversion rate resulting from the presence of 5 mole percent hydrogen in the initial charge of gases, a reaction rate of 2.2 gmole/l/hr vs 0.33 gmole/l/hr. This is a 6.7 fold increase in reaction rate.

Further Experiments

The following experiments delineated below demonstrate the patentable distinction between the instant invention and the process disclosed by Paulik et al in U.S. Pat. No. 3,769,329.

TABLE A

| Experiment | $Rh(CO)_2AcAc^{(a)}$ | $CH_3I$ | LiI | $CH_3OH$ | $CH_3OAc$ | $T^{(b)}$ | $P^{(c)}$ | CO Uptake$^{(c)}$ | Time (hours) | $H_2O^{(d)}$ |
|---|---|---|---|---|---|---|---|---|---|---|
| A | 8 | 64 | 0 | 50 | 100 | 180 | 800 | 1830 | 4 | 0 |
| B | 8 | 64 | 0 | 50 | 90 | 180 | 800 | 3000 | 0.5 | 10 g |
| C | 8 | 0 | 64 | 50 | 100 | 180 | 1000 | 4500 | 3.7 | 0 |
| D | 8 | 0 | 64 | 50 | 90 | 180 | 800 | 1030 | 4 | 10 g |

$^{(a)}$Rhodium carbonyl acetonylacetate
$^{(b)}$Temperature in °C.
$^{(c)}$Pressure in PSIG
$^{(d)}$Grams The data in Table A shows the following:

Experiment A represents Paulik's system using a Rh catalyst and $CH_3I$ promoter. The CO uptake of 1830 psig corresponds to 40.7% conversion of methanol in 4 hours.

Experiment B represents the effect of water addition on Paulik's system. The uptake of 3000 psig in 0.5 hours represents 67% conversion of methanol. Thus, the addition of water greatly accelerates the rate of conversion of methanol in Paulik's system.

Experiment C represents the instant system using a Rh catalyst and LiI as the promoter. In the absence of water the CO uptake was 4500 psig corresponding to 100% conversion of methanol in 3.7 hours.

Experiment D represents the effect of water on the instant system. The CO uptake was 1030 psig of CO in four hours representing only a 22.9% conversion of methanol.

It may be concluded from the above data that:
(1) In the process of Paulik et al, water significantly enhances the rate of conversion of methanol to acetic acid,
(2) In the instant process, water significantly retards the rate of conversion of methanol to acetic acid,
(3) The instant process is superior to that of Paulik et al and is distinct from Paulik et al.

TABLE B

| Experiment | $Rh(CO)_2AcAc^{(a)}$ | Iodine | $CH_3OH$ | $CH_3OAc$ | $T^{(b)}$ | $P^{(a)}$ | $CO^{(c)}$ | Time (hours) | $H_2O^{(d)}$ |
|---|---|---|---|---|---|---|---|---|---|
| E | 8 | 64(LiI) | 50 | 100 | 180 | 1000 | 4500 | 3.7 | 0 |
| F | 8 | 64(KI) | 50 | 100 | 180 | 1000 | 0 | 3.2 | 0 |
| G | 8 | 64(NaI) | 50 | 100 | 180 | 1000 | 500 | 3.2 | 0 |
| H | 8 | 64($CH_3I$) | 50 | 100 | 180 | 800 | 1830 | 4 | 0 |

$^{(a)}$Rhodium carbonyl acetonylacetate
$^{(b)}$Temperature in °C.
$^{(c)}$Pressure in PSIG
$^{(d)}$Grams The data in Table B demonstrates the following:

Experiment E represents the instant system using a Rh catalyst and LiI as the promoter. In the absence of water the CO uptake was 4500 psig corresponding to 100% conversion of methanol in 3.7 hours.

Experiment F represents the use of KI in place of LiI in the instant system. No CO uptake was observed and less than 1% acetic acid was found in the product.

Experiment G represents the use of NaI in place of LiI in the instant system-CO uptake of 500 psig was observed in 3.2 hours. This represents approximately 11% conversion of methanol.

Experiment H represents Paulik's system using a Rh catalyst and $CH_3I$ promoter. The CO uptake of 1830 psig corresponds to 40.7% conversion of methanol in four hours.

The following conclusions may be drawn from the data in Table B:

(1) KI is not a promoter for the carbonylation of methanol to acetic acid in an anhydrous system,
(2) NaI is an order of magnitude less efficient than LiI as a promoter for the carbonylation of methanol to acetic acid in an anhydrous system,
(3) NaI is even inferior to $CH_3I$ (Paulik's) system as a promoter for the carbonylation of methanol to acetic acid in an anhydrous system, (4) LiI is unique in its ability to efficiently promote the carbonylation of methanol in an anhydrous system.

The following experiments have been run to demonstrate the significant differences between the present invention using a rhodium catalyst with LiI and $CH_3I$ as prormoters in an anhydrous medium versus the Paulik system using a rhodium catalyst with a $CH_3I$ promoter with the addition of alkali metal halide promoters in an aqueous medium.

TABLE C

| Experiment | $Rh(CO)_2AcAc^{(a)}$ | $CH_3I$ | XI | $CH_3OH$ | $CH_3OAc$ | $T^{(b)}$ | $P^{(c)}$ | $CO^{(c)}$ Uptake | Time (hours) | $H_2O^{(d)}$ |
|---|---|---|---|---|---|---|---|---|---|---|
| I | 8 | | 0 | 50 | 100 | 180 | 800 | 1830 | 4 | 0 |
| J | 8 | | 0 | 50 | 90 | 180 | 800 | 3000 | 0.5 | 10 g |
| K | 8 | 0 | 64(LiI) | 50 | 100 | 180 | 1000 | 4500 | 3.7 | 0 |
| L | 8 | 0 | 64(LiI) | 50 | 90 | 180 | 800 | 1030 | 4 | 10 g |
| M | 4 | 32 | 32(LiI) | 50 | 100 | 180 | 650 | 4500 | 2.9 | 0 |
| N | 4 | 32 | 32(NaI) | 50 | 100 | 180 | 600 | 960 | 3.0 | 0 |
| O | 4 | 32 | 32(KI) | 50 | 100 | 180 | 700 | 3440 | 3.0 | 0 |
| P | 8 | 64 | 64(LiI) | 50 | 90 | 180* | 900 | 3200 | 0.42 | 10 |
| Q 12-14 | 8 | 64 | 64(KI) | 50 | 90 | 180 | 900 | 3100 | 0.53 | 10 |
| R 12-13 | 8 | 64 | 64(NaI) | 50 | 90 | 180 | 900 | 3100 | 0.45 | 10 |

$^{(a)}$Rhodium carbonyl acetonylacetate
$^{(b)}$Temperature in °C.
$^{(c)}$Pressure in PSIG
$^{(d)}$Grams
*Temperature was at 190° C. due to operator error for the initial five minutes of the run.

The data in Table C demonstrate the following:

Experiments P, Q, R which are Paulik-type systems employing Rh, $CH_3I$ and various alkali metal iodides give rates to acetic acid (as measured by CO uptake) equivalent to Experiment J which is Rh and $CH_3I$ without any additional metal iodide.

Experiment M is the instant system employing Rh, $CH_3I$, LiI in an anhydrous system. Although using half the Rh equivalents of comparable Example K, but the same total equivalents of halide (32 mmoles $CH_3I$ and 32 mmoles LiI), the rate to acetic acid (as measured by CO uptake) is significantly faster in Experiment M versus Experiment K.

Experiment N employing NaI versus LiI used in Experiment M but the same Rh and $CH_3I$ as Experiment N is significantly poorer than Experiment M in terms of the rate to acetic acid (as measured by CO uptake) in this anhydrous system.

Experiment O employing KI versus LiI or NaI used in Experiments M and N but the same Rh and $CH_3I$ as Experiments M and N was significantly better than Experiment N (using NaI) but inferior to Experiment M (using LiI) in terms of the rate to acetic acid (as measured by CO uptake) in an anhydrous system.

In summary, the rhodium catalysed carbonylation of methanol in an anhydrous system promoted by LiI is enhanced via use of a copromoter, $CH_3I$, ... comparison of Experiments M and K ... even though the total halide equivalents are constant. On an equivalent rhodium basis the LiI/$CH_3I$-promoted reaction rate is more than double the LiI only rate.

In Paulik's system the combination of $CH_3I$/XI where X=Li, Na, K, gives results identical to the use of $CH_3I$ alone. There is no beneficial effect manifested via the use of alkali metal halides with $CH_3I$ in Paulik's claimed system.

In the comparison of LiI/$CH_3I$, NaI/$CH_3I$ and KI/$CH_3I$ in the instant system, there was a difference found in the efficacy of the three promoters. LiI was found to be the best, followed by KI, with NaI a poor third.

The experimental findings are unexpected in view of the disclosure by R. T. Eby and T. C. Singleton in "Applied Industrial Catalysis", Vol I, Chapter 10, page 281, Academic Press, NYC (1983). In Chapter 10, entitled "Methanol Carbonylation to Acetic Acid", the authors state: "Iodide salts of alkali metals are inactive as catalysts in the rhodium-catalysed carbonylation of methanol, even though the $[Rh(CO)_2I_2]^-$ complex is formed in the presence of alkali metal iodides."

Lastly, it may be pointed out that even though readily apparent to those skilled in the art, a process which utilizes an anhydrous system (the instant invention) is superior commercially to an aqueous system (Paulik et al) in not requiring an expensive water removal step.

I claim:

1. A process for preparing an aliphatic carboxylic acid having from 2 to 6 carbon atoms which comprises reacting an aliphatic alcohol, having from 1 to 5 carbon atoms with carbon monoxide in the presence of a rhodium catalyst, methyl iodide, a lithium iodide content of at least about 0.2 moles per liter of reaction medium, the atomic ratio of iodide to lithium being greater than 1, a water content of less than about 12% by weight, and the ester of the aliphatic carboxylic acid and the aliphatic alcohol.

2. A process as claimed in claim 1 wherein the water content is from 0 to 6.5% by weight.

3. A process as claimed in claim 1 wherein the molar ratio of rhodium to aliphatic alcohol is in the range 1:40 to 1:2000 and the molar ratio of rhodium to lithium iodide is in the range 1:2 to 1:450.

4. A process as claimed in claim 3 wherein the molar ratio of rhodium to aliphatic alcohol is in the range 1:100 to 1:1000 and the molar ratio of rhodium to lithium iodide is in the range 1:8 to 1:150.

5. A process as claimed in claim 1 carried out in the presence of a ligand of formula $ER_3^{11}$ wherein E represents a Group VA element and $R^{11}$ represents hydrocarbyl or substituted hydrocarbyl groups.

6. A process for preparing acetic acid which comprises reacting methanol with carbon monoxide in the presence of a rhodium catalyst, methyl iodide, a lithium iodide content of at least about 0.2 moles per liter of reaction medium, the atomic ratio of iodide to lithium being greater than 1, a water content of less than about 12% by weight, and methyl acetate.

7. A process as claimed in claim 6 wherein the water content is from 0 to 6.5% by weight.

8. A process as claimed in claim 6 wherein the molar ratio of rhodium to methanol is in the range 1:40 to 1:2000 and the molar ratio of rhodium to lithium iodide is in the range 1:2 to 1:450.

9. A process as claimed in claim 8 wherein the molar ratio of rhodium to methanol is in the range 1:100 to 1:1000 and the molar ratio of rhodium to lithium iodide is in the range 1:8 to 1:150.

10. A process for preparing acetic acid which comprises reacting methanol with carbon monoxide in the presence of a rhodium catalyst, methyl iodide, a lithium iodide content of at least about 0.2 moles per liter of reaction medium, the atomic ratio of iodide to lithium being greater than 1, a water content of less than about 12% by weight, methyl acetate, and hydrogen.

11. A process as claimed in claim 10 wherein 2 to 10 mole percent hydrogen is present.

12. A process as claimed in claim 10 carried out in the presence of a ligand of formula $ER^{11}_3$ wherein E represents a Group VA element and $R^{11}$ represents an organic moiety.

13. A process for preparing acetic acid which comprises reacting methanol with carbon monoxide in the presence of a rhodium catalyst, methyl iodide, a lithium iodide content of at least about 0.2 moles per liter of reaction medium, the atomic ratio of iodide to lithium being greater than 1, a water content of less than about 12% by weight, and methyl acetate, and a ligand of formula $ER^{11}_3$ wherein E represents a Group VA element and $R^{11}$ represents the same of different hydrocarbyl or substituted hydrocarbyl groups.

14. A process as claimed in claim 1, wherein the molar ratio of rhodium to lithium iodide is in the range of 1:8 to 1:450.

15. A process as claimed in claim 6, wherein the molar ratio of rhodium to lithium iodide is in the range 1:8 to 1:450.

16. A process as claimed in claim 10 wherein the molar ratio of rhodium to lithium iodide is in the range 1:8 to 1:450.

17. A process as claimed in claim 10 wherein the water content is from 0 to 6.5% by weight.

* * * * *

UNITED STATES PATENT AND TRADEMARK OFFICE
CERTIFICATE OF CORRECTION

PATENT NO. : 5,281,751
DATED : January 25, 1994
INVENTOR(S) : DAVID J. SCHRECK

It is certified that error appears in the above-indentified patent and that said Letters Patent is hereby corrected as shown below:

Col. 5, l. 1, correct the spelling of the word "Catalytic"

Col. 7, l. 59, correct the spelling of the word "pentavalent"

Column 13,

Claim 16, line 1, there should be a comma (,) after "10,"

Signed and Sealed this

Twenty-sixth Day of July, 1994

Attest:

BRUCE LEHMAN

*Attesting Officer*    *Commissioner of Patents and Trademarks*